United States Patent [19]

Bailey, Jr.

[11] 4,378,108

[45] Mar. 29, 1983

[54] AUXILIARY SUPPORT TABLE FOR USE BY OPHTHALMOLOGISTS

[76] Inventor: Paul F. Bailey, Jr., 4885 NW. Barnes Rd., Portland, Oreg. 97210

[21] Appl. No.: 190,164

[22] Filed: Sep. 23, 1980

[51] Int. Cl.³ .............................................. A61G 13/00
[52] U.S. Cl. .................................................. 269/328
[58] Field of Search ................................ 269/322–328; 5/434, 435, 436, 437, 440, 442, 443, 444; 128/133, 134, 200.24

[56] References Cited

U.S. PATENT DOCUMENTS

| | | | |
|---|---|---|---|
| 535,945 | 3/1895 | Donald | 5/444 |
| 1,135,155 | 4/1915 | Blundell . | |
| 1,230,873 | 6/1917 | Crossley . | |
| 1,694,095 | 12/1928 | Moulin | 5/444 |
| 2,180,480 | 11/1939 | Richardson | 128/200.24 |
| 2,804,127 | 8/1957 | Whittingham | 5/440 |
| 2,963,247 | 12/1960 | Collier et al. . | |
| 3,188,079 | 6/1965 | Boetcher et al. | 269/328 |
| 3,319,954 | 5/1967 | Shevick et al. | 269/328 |
| 3,557,791 | 6/1971 | Duffy . | |
| 3,866,251 | 2/1975 | Pounds | 5/444 |
| 3,957,262 | 5/1976 | McReynolds | 269/328 |
| 4,018,217 | 4/1977 | Evans . | |

FOREIGN PATENT DOCUMENTS 178046 12/1964 U.S.S.R. .

Primary Examiner—Robert C. Watson
Attorney, Agent, or Firm—Kolisch, Hartwell & Dickinson

[57] ABSTRACT

An auxiliary table for use with an operating table to support a surgeon's hands during, for example, eye surgery includes a support table having a substantially planar upper surface for supporting the surgeon's hands. A mount detachably connected to the operating table holds the support table and enables the support table to be selectively oriented from a preoperative position remote from a patient's head to an operative position overlying the patient's head. Additionally, the mount includes a base and a pivot with the pivot interconnecting the base to the operating table for permitting the base to be angularly displaced, along with the support table, from the preoperative position to the operative position.

6 Claims, 6 Drawing Figures

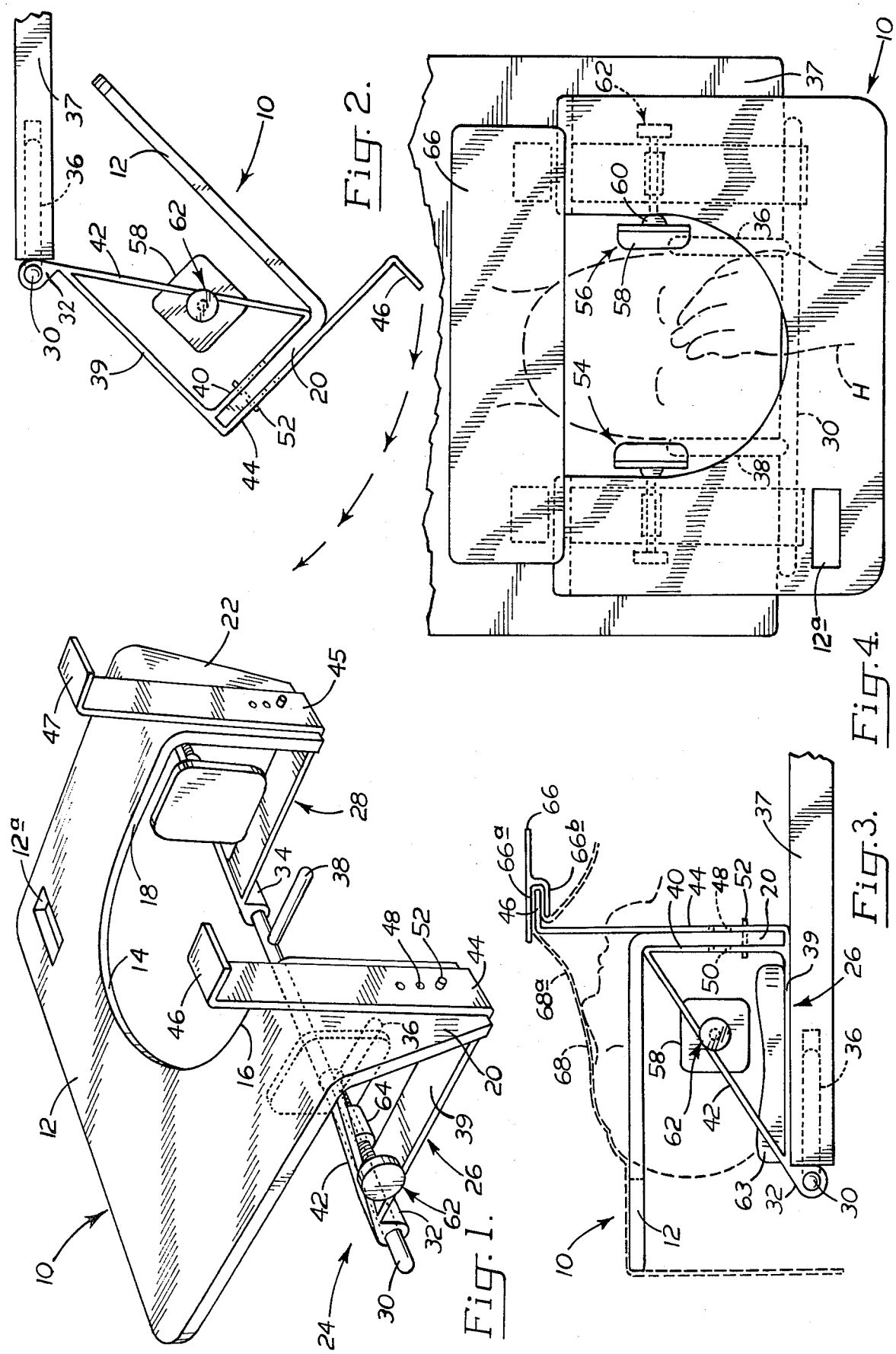

AUXILIARY SUPPORT TABLE FOR USE BY OPHTHALMOLOGISTS

BACKGROUND AND SUMMARY OF THE INVENTION

The present invention relates to surgical equipment such as operating tables, and more particularly to a novel auxiliary table which may be detachably mounted on an operating table for supporting a surgeon's hands during, for example, eye surgery. The auxiliary table is provided for stabilizing the ophthalmologist's hands and wrists and, if necessary, the forearms during eye surgery.

It is recognized that during delicate eye operations some type of support for the ophthalmologist's hands is highly advantageous. This is because surgical operations for cataracts, defective corneas, etc. are extremely minute and require delicate, precise hand movements by the ophthalmologist. An example of a prior art auxiliary table for use in microsurgery is set forth in U.S. Pat. No. 4,018,217, entitled "Arm and Hand Rest Device for Microsurgery". The patent discloses an arm and hand rest device which utilizes a horizontally disposed board for insertion between a patient's body and an operating table for retaining the device in a desired position with relation to the patient's body. A pair of separate tables are mounted on the horizontally disposed board and project upwardly therefrom located in a position adjacent the patient's head during an operation. Each of the tables includes means for vertical adjustment to different levels relative to one another. The surgeon's hands may be supported by the tables during eye surgery.

Another example of a device for use by an ophthalmologist is disclosed in the June, 1980, "Occutome/Fragmatome News Letter". The disclosure set forth in the news letter pictures and describes a so-called wrist rest and head rest combination for use by ophthalmologists to allow maximum clearance between the surgeon's knees and the operating table. Basically, the disclosure set forth in the news letter includes an arcuate, bar-like wrist rest which is adjustably mounted in a vertical direction on a head rest. Projecting from the head rest are elongate members for insertion into corresonding aligned bores in an operating table.

While it is recognized that supporting devices, such as described above, are advantageous, nonetheless such devices are deficient from a number of points. By way of explanation, preparing a patient for eye surgery requires that the patient initially be placed or rolled onto an operating table. During positioning of the patient, it is apparent that an auxiliary table must be positioned remote from the patient in order to prevent the patient from contacting the auxiliary table. Additionally, it should be recognized that a patient will be "draped" during an eye operation—this refers to the placing of a protective drape over the patient's head and body which is provided with an aperture for permitting access to the subject eye. It may be appreciated that the drape will tend to cling to the patient's body and head and in particular to areas around the patient's nose and mouth. Should the patient be under "local" anesthesia, the drape may interfere with normal breathing. If the patient is under a "general" anesthesia, the anesthesiologist needs to regulate and monitor the patient's breathing through the use of a tracheal tube during the duration of surgery.

In either case, it is necessary for room to be provided between the bottom of the drape and the patient's nose and mouth region, i.e. under local anesthesia, the patient must have breathing room, and under general anesthesia sufficient free space must be available between the bottom of the drape and the patient's nose and mouth region so that the surgeon may adjust and monitor the tracheal tube. With prior art head rest devices, as well as during operations not utilizing an auxiliary arm and hand rest, the anesthesiologist or nurse must manually pick up or elevate the drape adjacent the patient's nose and mouth in order to provide the required space.

Additionally, draping of the patient also creates another problem, namely: the drape, tending to cling to the patient's head, forms a curved surface so that liquids administered to the eye during operation tend to flow off the curved surface and drip to the floor of the operating room causing a slippery surface. This situation obviously presents a dangerous circumstance because the ophthalmologist and the various attendants may slip and fall.

The present invention seeks to overcome the above problems, amongst others. Accordingly, it is an object of the present invention to provide a novel auxiliary table for use with an operating table comprising a support means having a substantially planar upper surface for supporting a surgeon's hands which is connected to the operating table by a mounting means secured to the support means. The mounting means enables the support means to be selectively oriented or shifted from a preoperative position remote from a patient's head to an operative position overlying the patient's head. The selective orientation may take place while the auxiliary table is maintained in a mounted position on the operating table. More particularly, the auxiliary table is constructed so that the mounting means includes a base means provided with pivot means so that the base means (secured to the support means) may be angularly displaced from the preoperative position to the operative position, whereby the base means engages the operating table for being supported thereon.

Another object of the present invention is to provide an auxiliary table, as described above, in which the pivot means includes a rod means from which projecting means or "fingers" extend for detachable inserting into bore means provided in an end of the operating table. The base means is provided with sleeve means for rotatably receiving the rod means so that the base means, together with the support means, may be pivoted downwardly beneath the upper surface of the operating table, adjacent an end thereof, so that an entirely free area is presented on the operating table. The patient may then be rolled onto the operating table without any impediment from the auxiliary table. The mounting means and support means may be angularly displaced upwardly along an arcuate path so as to be positioned in the operative position overlying the patient's head.

Still another object of the present invention is to provide an auxiliary table, as described above, in which the base means is provided with an upstanding member extending generally upright therefrom above the planar upper surface of the support means for enabling a drape positioned over the patient's head to be elevated above the patient's nose and mouth region.

A still further object of the present invention is to provide an auxiliary table, as described above, in which an instrument tray may be detachably mounted on the upstanding member in proximal location to the ophthalmologist's hands. The tray is provided for carrying surgical instruments or the like.

These and additional objects and advantages of the present invention will be more completely understood from a consideration of the drawings and the following detailed description of the preferred embodiment.

BRIEF DESCRIPTION OF THE DRAWINGS

FIG. 1 is a perspective view of an auxiliary table in accordance with the present invention illustrating its components prior to the auxiliary table being positioned for connection with an operating table;

FIG. 2 is a side elevation view of the auxiliary table of the present invention after it has been mounted on an operating table (only a portion of which is shown) with the auxiliary table being disposed in a preoperative position;

FIG. 3 is a view similar to FIG. 2 illustrating orientation of the auxiliary table from its preoperative position shown in FIG. 2 to an operative position overlying a patient's head with the patient being shown in phantom lines;

FIG. 4 is a top plan view of FIG. 3;

DETAILED DESCRIPTION OF THE PREFERRED EMBODIMENT

Figure 5:
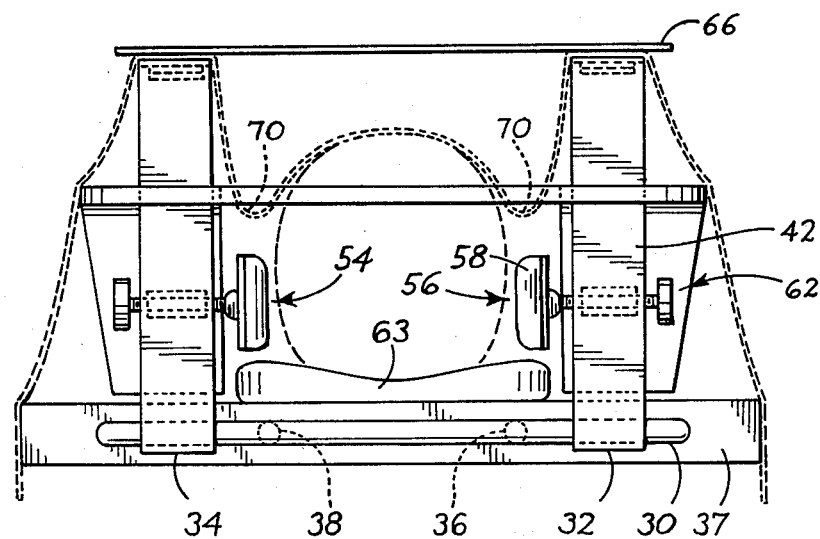
FIG. 5 is an end view of the auxiliary table of the present invention looking in from an end of the operating table.

Turning now the the drawings, attention is initially directed to FIG. 1 which illustrates in perspective view, an auxiliary table according to the present invention generally indicated at 10. The auxiliary table includes a table or support means 12 having a substantially planar upper surface for supporting a surgeon's hands. An arcuate interior periphery dimensioned for generally surrounding a patient's head is formed in support means 12 and is indicated at 14. The periphery extends toward generally rectilinear interior edges indicated at 16, 18 and leg means are indicated at 20, 22. The leg means extend generally perpendicularly downwardly from the upper planar surface and are connected to a mounting means generally indicated at 24. It is contemplated that support means 12 may be formed of any suitable material such as heavy plastic, which has been found to be advantageous.

Considering now a description of mounting means 24, it is to be noted that the mounting means is adapted for connection to an operating table and is secured to the support means for enabling it to be selectively oriented from a preoperative position remote from a patient's head to an operative position overlying the patient's head. To this end, mounting means 24 includes a pair of base means indicated generally at 26, 28, and a pivot means. The pivot means includes an elongate rod means shown at 30 which is rotatably received within a pair of aligned sleeves 32, 34 provided on base means 26, 28 respectively. The rod means is provided with projecting means or fingers, indicated at 36, 38 extending generally perpendicularly therefrom for detachable inserting into bores provided in an operating table. Generally, such bores are normally provided in one end of an operating table for receiving attachments such as operating table extensions, etc.

With respect to a description of the base means, attention is directed to FIGS. 2 and 3, as well as FIG. 1. As shown in FIGS. 2 and 3, the fingers such as finger 36 have been suitably inserted into side-by-side positioned bores provided in an operating table indicated at 37 (only a portion of the operating table being shown). As shown in FIG. 3, base means 26 (base means 28 being substantially similar) includes a plate 39 which is mounted adjacent sleeve 32 for being supported on operating table 37. An upright 40 extends upwardly from plate 38 and a brace or strut is indicated at 42. Spaced apart from plate 40 and forwardly thereof, as shown in FIG. 3, is an upstanding member 44.

The upstanding member includes a ledge means indicated at 46. As can be seen from a consideration of FIG. 3, leg means 20 of support means 12 is slideably inserted into the space between upright 40 and upstanding member 44. This space may be thought of as a guide means provided on the base means for receiving leg means 20. Additionally, leg means 20 may also be secured to the guide means, and more particularly to upright 40 and upstanding member 44 (an upstanding member 45 being shown provided with base means 28 also includes a ledge means 47). Explaining further, upright 40 and upstanding member 44 are provided with a plurality of aligned bores such as indicated at 48, 50. A retaining means such as a removable pin is shown at 52 inserted through a pair of the aforementioned aligned bores as well as through a bore provided in leg means 20. Thus, it can be appreciated that leg means 20 (as well as leg means 22) may be shifted in its associated guide means for being selectively positioned therein. It may be desired to raise or lower the upper surface of support means 12 relative to a patient's head depending upon the dimensional characteristics of a patient's head and/or surgeon perference.

Additionally, it is to be noted that head stabilizing means are provided on each of the base means so that a head may be stabilized when auxiliary table 10 is disposed in the operative position. In further explanation, reference is directed to FIGS. 4 and 5 as well as FIG. 3 which illustrate the use of a pair of stabilizing means generally indicated at 54, 56. Considering stabilizing means 56 (stabilizing means 54 being substantially similar), it can be seen that it includes a resilient pad member 58 provided with a collar 60. A thumb screw indicated at 62 (see also FIG. 1) includes a threaded rod which engages threads provided in a sleeve 64 mounted on brace 42. Collar 60 is connected to an end of the thumb screw but permits the thumb screw to rotate relative thereto. Thus, depending upon clockwise or counterclockwise rotation of the thumb screws, the resilient members may be shifted toward or away from opposite sides of a patient's head for engagement thereagainst so as to stabilize the head relative to the base and support means or for positioning away from the head.

A description of how auxiliary table 10 of the present invention is used during eye surgery will now be set forth. Reference is directed again to FIG. 1 as well as in particular to FIG. 2. Before a patient is placed on operating table 36, auxiliary table 10 (assumed to be detached from the operating table) is carried by an orderly or a nurse to a position adjacent the end of the operating table which includes the aforementioned side by side positioned bores. With auxiliary table 10 held in the position somewhat similar to that shown in FIG. 2, fingers 36, 38 are inserted into the bores in the operating table. The auxiliary table may be permitted to hang freely as shown in FIG. 2 and a patient is then placed or rolled onto the operating table. As can be appreciated, with auxiliary table 10 hanging as shown, it is remote from the patient and will not present an impediment to the placing and shifting of the patient onto the operating table.

Next, a head rest, such as shown at 63 in FIGS. 3 and 5, is placed beneath the patient's head. With stabilizing means 54, 56 moved outwardly, auxiliary table 10 is then pivoted in a clockwise direction, as shown in FIG. 2, until the base means engage the operating table for being supported thereon such as shown in FIG. 3. Next, each of the thumb screws for shifting its associated resilient member, such as thumb screw 62 operable for shifting resilient member 58, are actuated so as to urge the resilient members against the side of the patient's head. The patient's head is then stabilized relative to the auxiliary table. It may then be desired to shift support means 12 relative to the base means to a preselected position by suitably positioning pin means 52 in corresponding appropriate bores such as bores 48, 50, etc.

It is now necessary to "drape" the patient and a suitable drape is positioned over the patient's body and head. An instrument tray, indicated at 66 in FIGS. 3–6 is not, at this point, mounted on the auxiliary table as shown in FIG. 3. The drape, shown at 68 in FIG. 3 is placed over the patient's body, over ledge means 46, 47 and over the patient's facial frontal area as shown. The drape is provided with a suitable aperture for isolating the eye upon which the operation is to take place. The drape hangs over support means 12 as shown in FIG. 3. Tray 66 which includes a pair of spaced-apart "clip" members 66a, 66b may then be clipped onto the ledge means such as ledge means 46 shown in FIG. 3. The clipping action requires that the drape be positioned between the clip members and the top and bottom portions of ledge means 46 in a serpentine manner as illustrated.

As can be seen from a consideration of FIG. 3, the drape, being held upwardly by upstanding member 44 and ledge means 46 (as well as by upstanding member 45 and ledge means 47) is elevated above the patient's nose and mouth area. Thus, the upstanding member which extends generally upright from the base means may be thought of as a drape positioning means extending above the planar upper surface of support means 12 for maintaining a portion of the drape elevated above the patient's nose and mouth area.

Figure 6:
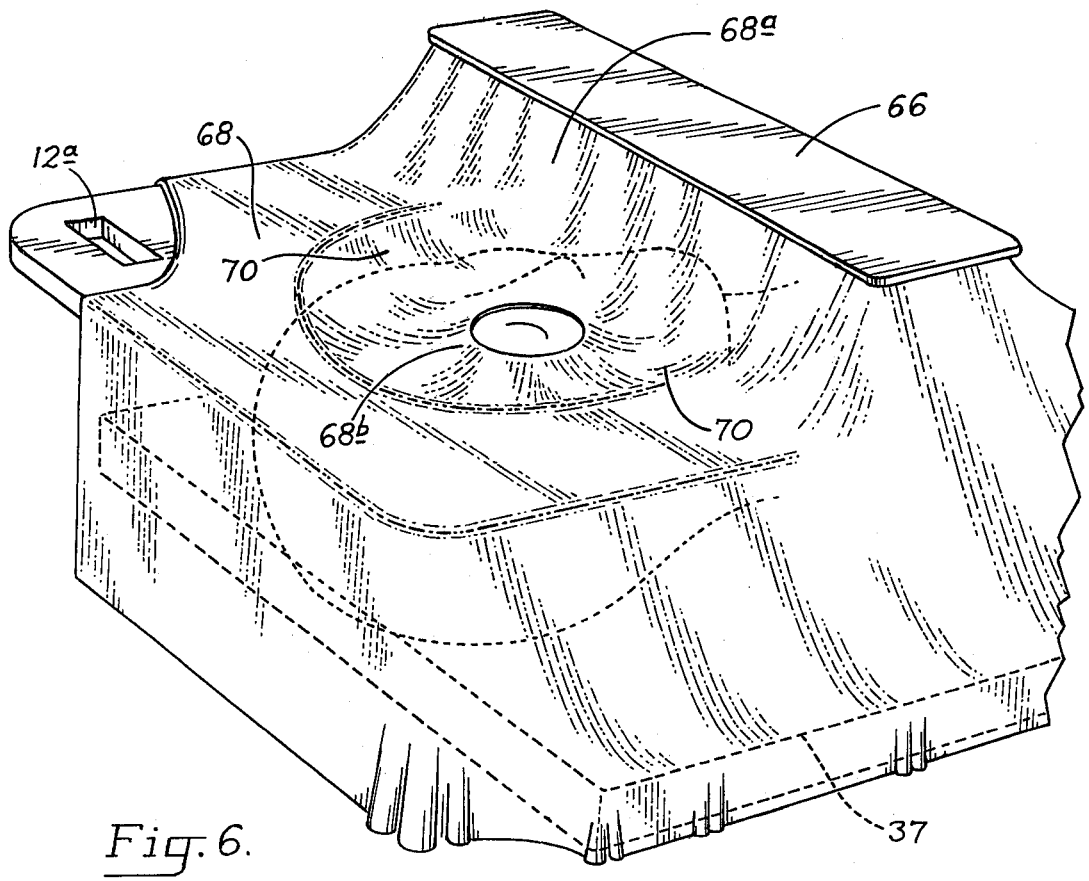
FIG. 6 is a perspective view illustrating positioning of a patient drape on the auxiliary table.

As shown in FIG. 6, another significant advantage of the construction of the auxiliary table, when used in conjunction with a drape, is apparent. For instance, it can be seen that drape 68 with portion 68a disposed above a patient's nose and mouth area may also be "tucked in" around the sides of a patient's head so as to form a trough extending downwardly from the interior periphery of support means 12. This trough is indicated at 70 in FIGS. 5 and 6 and serves to catch and retain any fluid which may flow from the patient's eye during the operation. Such fluids may include saline solutions which are administered periodically to the eye by a "dripper". It can be appreciated that trough 70 is an annular trough and will retain the fluid in the depression therein formed in the drape. As shown in FIG. 6, an operation on the right eye of the patient is to be performed with a suitable aperture indicated at 68b being provided in drape 68.

Tray 66 is in ready position for access by a surgeon during the operation. The tray may be used for holding surgical instruments, the "dripper" and other necessary items. A surgeon's hand is shown in phantom lines at H in FIG. 4 positioned on top of support means 12 (the other hand is not shown). After the operation, the tray is removed, the drape pulled away and auxiliary table 10 may be pivoted from its operative position to the preoperative position shown in FIG. 2 (now a postoperative position). The patient may then be removed for postoperative care. It should also be noted that support means 12 may be provided with suitable recesses or openings, such as shown at 12a for holding microscope controls, etc.

From the above description, it should be apparent that the auxiliary table of the present invention provides several important and distinct advantages. First of all, the auxiliary table which includes support means 12 and mounting means 24 may be selectively oriented from a preoperative position remote from a patient's head (as shown in FIG. 2) to an operative position overlying the patient's head. This selective orientation is accomplished by use of a pivot means including rod means 30 which is connected to base means 26, 28. With rod means 30 being provided with fingers 36, 38, the auxiliary table may be readily mounted on and detached from an conventional operating table. The planar upper surface of support means 12 provides a comfortable surface against which a surgeon may find support for the hands, wrists and forearms if needed while performing delicate eye surgery. Additionally, because support means 12 is provided with leg means, such as indicated at 20, 22, inserted in corresponding guide means, the upper planar surface of the support means may be selectively adjusted to a preselected height relative to a patient's head. This is accomplished by suitable insertion of pin means, such as pin means 52 in selected aligned apertures in upright 40 and upstanding member 44.

A particularly advantageous component of the present invention is the provision of upstanding members such as indicated at 44, 45 provided with associated ledge means 46, 47 respectively. The upstanding members serve as a drape positioning means extending above the planar upper surface of support means 12 for elevating and maintaining a portion of the drape above the patient's nose and mouth area. Of course, as mentioned previously the elevation of the drape concomitantly enables "tucking in" of the drape for forming of a trough around the patient's head adjacent the interior head receiving periphery of support means 12.

A still further advantage of the present invention is the provision of the stabilizing means, such as indicated at 54, 56 mounted on corresponding base means. A patient's head may be stabilized, in a comfortable manner, so that any inadvertent shifting of the patient may be prevented. This particularly is important during delicate eye surgery which may involve corneal surgery, as well as cataract operations.

While the present application has been described with reference to the foregoing preferred embodiment, it will be appreciated by those skilled in the art that other changes in form and detail may be made therein without departing from the spirit and scope of the present invention as defined in the appended claims.

It is claimed and desired to secure by Letters Patent:

1. An auxiliary table for use with an operating table to support a surgeon's hands during, for example, eye surgery, comprising:

support means having a substantially planar upper surface for supporting the surgeon's hands; and mounting means connected to the operating table including a base means for carrying said support means and for enabling said support means to be selectively oriented from a preoperative position remote from a patient's head to an operative position overlying the patient's head;

said mounting means also including pivot means interconnecting said base means to the operating table for permitting said base means to be angularly displaced from said preoperative position to said operative position whereby said base means engages the operating table for being supported thereon;

said pivot means including rod means for detachable connecting to the operating table, said base means being provided with sleeve means for rotatably receiving said rod means, said rod means including projecting means extending therefrom for detachable inserting into bore means provided in the operating table so that said rod means may be nonrotatably mounted relative to the operating table.

2. The auxiliary table of claim 1 wherein said support means includes leg means extending generally perpendicularly therefrom, said base means including guide means for receiving and securing said leg means thereto.

3. The auxiliary table of claim 2 wherein said base means further includes drape positioning means extending above said planar upper surface of said support means for maintaining a portion of a patient drape elevated above the patient's nose and mouth area.

4. The auxiliary table of claim 3 wherein said drape positioning means includes an upstanding member extending generally upright from said base means and disposed adjacent said guide means.

5. The auxiliary table of claim 4 further including an instrument tray detachably mounted on said upstanding member for carrying surgical instruments and the like, said upstanding member including ledge means for receiving and holding said instrument tray.

6. The auxiliary table claim 4 wherein said base means includes head positioning means adjustably mounted thereon, said head positioning means including a pair of resilient members disposed on said base means adjustable toward opposite sides of the patient's head for engagement thereagainst so as to stabilize the patient's head relative to said base means and said support means.

* * * * *